United States Patent [19]

Pellicciari et al.

[11] Patent Number: 5,166,374

[45] Date of Patent: * Nov. 24, 1992

[54] BILE ACID DERIVATIVES, PROCESSES FOR THE PREPARATION THEREOF AND PHARMACEUTICAL COMPOSITIONS CONTAINING THEM

[75] Inventors: Roberto Pellicciari; Aldo Roda; Giuliano Frigerio, all of Milan, Italy

[73] Assignee: Giuliani S.P.A., Milan, Italy

[*] Notice: The portion of the term of this patent subsequent to Oct. 15, 2008 has been disclaimed.

[21] Appl. No.: 761,441

[22] Filed: Sep. 18, 1991

Related U.S. Application Data

[63] Continuation-in-part of Ser. No. 507,260, Apr. 9, 1990, Pat. No. 5,057,509.

[30] Foreign Application Priority Data

Apr. 17, 1989 [IT] Italy .................................. 20169A/89

[51] Int. Cl.$^5$ ................................................ C07J 9/00
[52] U.S. Cl. .................................................... 552/542
[58] Field of Search ..................................... 552/542

[56] References Cited

U.S. PATENT DOCUMENTS 5,057,509 10/1991 Pellicciari et al. ................... 552/542

Primary Examiner—Marianne M. Cintins
Assistant Examiner—Kimberly J. Kestler
Attorney, Agent, or Firm—Walter H. Schneider

[57] ABSTRACT

Compounds of general formula I

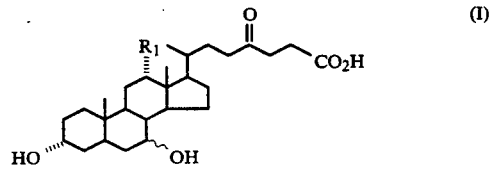

wherein $R_1$ is hydrogen or hydroxy, and the hydroxy group at the 7-position can be either in $\alpha$ or $\beta$ configuration, are valuable in human therapy. Compounds I can be prepared by reacting with succinic acid carboanions the corresponding derivatives which have previously been protected, and subsequently deprotecting and decarboxylating them.

1 Claim, No Drawings

BILE ACID DERIVATIVES, PROCESSES FOR THE PREPARATION THEREOF AND PHARMACEUTICAL COMPOSITIONS CONTAINING THEM

This application is a continuation-in-part of appl. Ser. No. 507,260 filed Apr. 9, 1990, now U.S. Pat. No. 5,057,509.

The present invention relates to bile acid derivatives, to a process for the preparation thereof and to pharmaceutical compositions containing them.

The derivatives of the present invention have the following general formula I

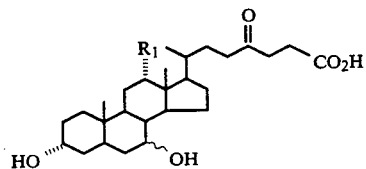

wherein $R_1$ is hydrogen or hydroxy, and the hydroxy group at 7-position can be either in $\alpha$ or $\beta$ configuration.

Therefore, compounds I are the derivatives of the following natural bile acids: ursodeoxycholic (UDCA) (3$\alpha$, 7$\beta$ OH), ursocholic (3$\alpha$, 7$\beta$ OH; $R_1$=OH), chenodeoxycholic (3$\alpha$, 7$\alpha$ OH) and cholic (3$\alpha$, 7$\alpha$ OH; $R_1$=OH) acids.

The present invention also relates to the physiologically acceptable salts of compounds I, as well as to the single isomers or diastereoisomers of compounds I and to the mixtures thereof.

The above cited bile acids have been used for a long time in human therapy for the treatment of biliary calculosis, as antidyspeptic, eupeptic, antidyslipidemic and choleretic agents, and generally in all those pathological logical conditions in which a stimulation of bile flow and a qualitative and/or quantitative change thereof are required.

Therapeutic characteristics of natural molecules promoted the development of a number of synthetic or semi-synthetic derivatives in the attempt to obtain improved drugs as regard pharmacokinetic, metabolic or chemico-physical aspects (lipophilia/hydrophilia ratio, stability, critical micellar concentration). See, for instance, EP-A-83106708.7, 84104598.2, 84109811.4, 85115611.7.

Now it has been found that compounds of formula I, which can be considered the structural analogs of bile acid glyconjugated derivatives in which the —NH— group has been replaced by a CH$_2$ group, have valuable pharmacological characteristics, such as an improved intestinal absorption as well as an increased bile excretion, without requiring the in vivo conjugation. The compounds of the invention, moreover, are characterized by an increased lasting action and by a very poor toxicity (LD$_{50}$ per os in the mouse lower than 5 g/kg).

Therefore, compounds of formula I or the non toxic salts thereof are valuable as anticholestatic, choleretic, antidyslipemic and hepatocyte-protecting agents, in addition to the up to now conventionally known uses of bile acids, i.e. for the treatment of cholelithiasis, bile desaturation, metabolic control of cholesterol, and the like.

The compounds of the invention, for the envisaged therapeutic uses, are administered in form of pharmaceutical compositions prepared according to known techniques and excipients, as described e.g. in "Remington's Pharmaceutical Sciences Handbook", Hack Pub. Co.,N.Y. USA.

The preferred administration route is the oral one, and the daily doses, which will vary depending on the pathology to be treated and the patient's conditions, will in principle be comprised from 50 mg to 1 g, one or more times a day.

Examples of suitable pharmaceutical compositions comprise capsules, tablets, sugar-coated pills, syrups, granulates, solutions, vials. The compounds of the invention can also be administered by local perfusion, before or after surgical operations, in form of dispersible solutions or powders.

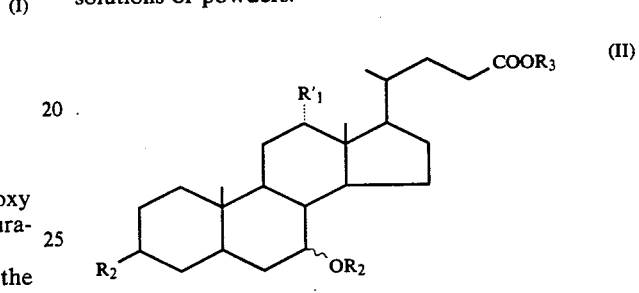

Compounds I are prepared by reacting compounds II, in which $R_2$ is a hydroxy protecting group, $R'_1$ is hydrogen or a protected hydroxy group, $R_3$ is a carboxy protecting group, with succinic acid or a reactive derivative thereof in the presence of bases which can form the CH-anion on one of the two methylene groups of succinic acid, followed by decarboxylation of the carboxy or alkoxycarbonyl group in to the carbonyl group.

A preferred succinic acid derivative is the anhydride, but other derivatives, such as the esters or the hemiesters, can conveniently be used.

Suited bases are alkali and alkali-earth metal alkoxides, lithium alkyls and lithium amides.

The reaction with succinic acid or the reactive derivative thereof is carried out in the presence of at least stoichiometric amounts of said bases, in the presence of anhydrous inert solvents such as ethers (dioxane, tetrahydrofuran, ethyl ether), hydrocarbons (hexane, benzene, toluene), or halogenated hydrocarbons. The reaction is preferably carried out under inert gas atmosphere (nitrogen, argon, helium), at low temperatures from $-30°$ to $-100°$ C., preferably at $-45°$ to $-80°$ C., according to known techniques conventionally used for this kind of reactions. Remotion of the protecting groups and decarboxylation finally lead to the compounds of the invention.

Suitable hydroxy protecting groups are esters, such as acetates, trichloroacetates, formates, benzoates, benzyloxy carbonyl derivatives, carbonates; ethers such as tetrahydropyranyl ethers, silyl deerivatives and the like. Suitable carboxy protecting groups are esters such as methyl, t-butyl, benzyl, benzhydryl, trityl, p-bitrobenzyl, trimethylsilyl and tetrahydropyranyl esters, amides, hydrazides and the like.

Although all the known protective groups can be used as far as they are inert under the selected reaction condition, the acetic ester is preferred as the hydroxy protecting group and the methyl ester is preferred as the carboxy protecting group.

The following example further illustrates the invention.

EXAMPLE 1

Preparation of 3α, 7β-dihydroxy-24-oxo-5β-cholan-27-oic acid.

a) methyl 3α, 7β-dicatyloxy-5β-cholanoate.

Ethyl chloroformate (13.2 ml, 137.9 mmol) was added dropwise during 30 minutes to a solution of methyl 3α, 7β-dihydroxy-5β-cholanoate (7.0 g, 17.22 mmol) in anhydrous dioxane (175 ml) containing pyridine (11.2 ml, 137.9 mmol), which solution was kept at 0° C., under strong mechanical stirring. At the end of the addition the mixture was left to warm to room temperature and mechanical stirring was continued overnight. Then the reaction mixture was poured into water/ice (350 ml) and extracted with ether (4×70 ml). The combined organic phases were washed with 10% hydrochloric acid (2×50 ml) and dried over anhydrous sodium sulfate. After evaporation of the solvent, the residue (10 g) was subjected to flash chromatography, eluting with petroleum ether-ethyl acetate 8:2, to obtain 8.7 g (92%) of pure product.

b) 3α, 7β-dicatyloxy-23-carbomethoxy-24-oxo-5β-cholan-27-oic acid.

A solution of the product obtained in step a) (0.55 g, 1.0 mmol) in tetrahydrofuran (10 ml) was cooled to −78° C. and added dropwise, during 10 minutes, to a lithium-diisopropylamide solution obtained by addition of a n-butyl lithium hexane solution (1.1 ml of a 1.14 M solution) to a diisopropylamine solution (0.13 g, 1.21 mmol) in tetrahydrofuran (25 ml) kept at −78° C. under strong magnetic stirring under argon atmosphere. 45 Minutes after the end of the addition, the mixture was added dropwise with a succinic anhydride solution (0.12 g, 1.2 mmol) in tetrahydrofuran (10 ml) previously cooled to −78° C., during 10 minutes. At the end of the addition, the reaction mixture was left to warm to room temperature, then it was poured into a 10% hydrochloric acid solution (100 ml) and extracted with ether (5×25 ml). The combined organic phases were extracted with a 2.5% sodium hydroxide solution (3×30 ml); then the agueous phase was acidified with conc. hydrochloric acid and extracted again with ether (3×30 ml). The combined ether extracts were washed with brine (2×30 ml) and dried over sodium sulfate. After evaporation of the solvent, 0.27 g of a crude product were obtained, which was directly used in the subsequent reaction.

c) 3α, 7β-dihydroxy-24-oxo-5β-cholan-27-oic acid.

Potassium hydroxide (5.0 g) was added to a solution of the above crude product (2.0 g) in methanol (50 ml) and water (10 ml) and the resulting mixture was refluxed for 1 hour. After cooling, the mixture was poured into ice-water (200 ml), acidified with conc. hydrochloric acid and extracted with ethyl acetate (4×50 ml) and dried over sodium sulfate. After evaporation of the solvent, the residue (1.4 g) was subjected to flash chromatography, eluting with chloroform-methanol-acetic acid 80:20:0.1 (v/v/v) to obtain 0.8 g of the pure product, m.p. 79°–82° C. (total yield 3:18%), the structure of which was confirmed by $^1$H-NMR, $^{13}$C-NMR and mass spectrometry.

PHYSICOCHEMICAL AND BIOLOGICAL PROPERTIES OF 24-ISOP ANALOG.

The properties of the ursodeoxycholic acid derivative of formula (I), which hereinafter will also be referred to as 24-ISOP, have been studied and compared with those of natural analogs UDCA, glycoursodeoxycholic and tauroursodeoxycholic acid since these are present in the organism after chronic administration of UDCA.

Physicochemical properties

The 24-ISOP acid must present some peculiar and foundamental characteristics in aqueous solution for the use as new analog of UDCA.

In particular, it should have a low detergency and lipophilicity and a good solubility at a pH 5-8 also in micellar solutions.

The following characteristics:
-critical micellar concentration (CMC) or "detergency",
-lipophylicity,
-solubility,
-critical micellar pH
were evaluated according to conventional methods.
Critical micellar concentration.

The structural modification of the side chain does not change the detergency of the molecule.

The CMC value is similar to glycoursodeoxycholic and tauroursodeoxycholic acid and slightly lower than that of unconjugated UDCA.

The values are reported in Table I.

Lipophilicity

The structure of the side chain influences the lipophilicity of the molecule in ionic form which presents intermediate values between the unconjugated and conjugated forms of UDCA.

Acidity constant

The pKa value of 24-ISOP (4.2) is much lower than that of UDCA (pKa 6) and similar to that of glycoursodeoxycholic acid (3.9).

Solubility

This molecule presents low solubility at low pH like UDCA or glycoUDCA but the high acidity constant causes resistance to precipitation at relatively low pH when the acid is present ionized and in micellar form (low critical micellar pH).

Liver uptake and intestinal metabolism

When 24-ISOP acid is administered intravenously it is rapidly taken up by the liver and secreted into bile. The molecule is completely recovered in bile with a rapid kinetic and no significant metabolites are present. In comparison UDCA is completely transformed into its conjugated form, tauroursodexycholic acid and to less extent into glycoursodeoxycholic acid.

The kinetic of the biliary secretion is very fast in comparison with UDCA and more similar to tauroursodeoxycholic acid.

At the end of the infusion, 24-ISOP disappears from bile with a kinetic similar to conjugate forms of UDCA and faster than UDCA.

When administered intraduodenally, 24-ISOP is efficiently absorbed and the recovery in bile is significantly higher than that of glycoursodeoxycholic and similar to UDCA and TUDCA.

Also after i.d. administration no major metabolites are present.

When 24-ISOP is incubated with human fresh stools in aerobic and anaerobic conditions the molecule is partially metabolized (7-dehydroxylated) with a kinetic significantly lower the UDCA and its conjugated forms. Effects on bile flow and biliary lipid secretion.

The intravenously administration of 24-ISOP acid causes a great effect on bile flow, higher than that of UDCA and its conjugated forms. (Table II)

There are no significative differences on the transport and secretion of cholesterol and phospholipids in respect to the physiologic analogs (Table II).

The 24-ISOP analog of UDCA has interesting physicochemical properties in aqueous solution as a result of the presence of an oxo-group on the side chain. The side chain configuration and conformation is optimal for micelle formation since the CMC values are similar to the natural conjugated analogs.

As far as the lipophylicity is concerned, the presence of an oxo group in the side chain decreases the lipophilicity of the molecule in comparison with the unconjugated UDCA.

When compared with amidated UDCA with the same number of C-atoms on the side chain and with an amide bond the lipophilicity is slightly higher.

Finally the solubility of the protonated form is quite low but the low pKa and relatively low CMC make this analog soluble when present in micellar form at a pH lower than UDCA (low CMpH).

These peculiar physicochemical and structural properties give to 24-ISOP unique pharmacokinetic characteristics:

a) 24-ISOP is absorbed by the liver and promptly secreted into bile without need of conjugation with glycine or taurine;
b) when infused intraduodenally it is well absorbed by the intestine even better than some natural analogs, like glycoursodeoxycholic acid, and
c) the rate of its intestinal metabolism and particularly its 7-dehydroxylation is very low when compared with UDCA;
d) when administrered either i.v. or i.d., 24-ISOP shows an high choleretic effect, higher than that of UDCA.

The optimal combination of the above mentioned physicochemical and biological properties gives to this new analog promising characteristics for a better conservation in the entero heparic circulation in comparison with UDCA and consequently greater improvement when used as a drug for both cholesterol gallstone dissolution or cholestatic syndromes.

TABLE I

Physicochemical properties of 24-ISOP in comparison with UDCA, GUDCA and TUDCA

| Bile acids | CMC (mM) | K' | Solubility' (μM) | pKa |
|---|---|---|---|---|
| UDCA | 19 | 3.66 | 9 | 5.06 |
| TUDCA | 8 | 0.98 | — | 2 |
| GUDCA | 12 | 1.06 | 3 | 3.90 |
| 24-ISOP | 9 | 2.12 | 20 | 4.2 |

K' = calculated from retention times (t) on C-18 HPLC according to $$K = \frac{t_{AB} - t_o}{t_o}$$

where $t_o$ = time of unretained solvent, under the following conditions: $CH_3OH/KH_2PO_4$ 0.01 M 130/70 v/v pH = 7.

TABLE II

Effect of 24-ISOP on bile flow and biliary secretion when administered i.v. to rat. Comparison with natural analogs

| | $SMV_o$ μl/min/kg | $SM_{AB}$ | SMxol μmol/min/kg | $SM_{FL}$ |
|---|---|---|---|---|
| UDCA | 60 | 3.02 | 0.022 | 0.227 |
| TUDCA | 36 | 3.40 | 0.014 | 0.18 |
| GUDCA | 40 | 2.10 | 0.028 | 0.39 |
| 24-ISOP | 87 | 2.62 | 0.020 | 0.21 |

$SV_o$ = mean maximum bile flow.
SM = mean maximum biliary lipid secretion.
354.4 (2.64%). $C_{24}H_{39}FO_4$.

EXAMPLE 2

Preparation of 3α, 7β, 12α-Trihydroxy-24-oxo-5β-cholan-27-oic acid. (24-PUCA)

Methyl ursocholate was submitted to reaction with ethyl chloroformate in pyridine to give the corresponding cathyl derivative with 50% yield. This protected ester was then reacted with lithium diisopropylamide followed by treatment with succinic anhydride in THF at −78° C. yielding the corresponding 3α-7β-12α-tricathyloxy-23-carbomethoxy-24-oxo-5β-cholan-24-oic acid, which was then decarboalcoxylated to give the 3α-7β-12α-trihydroxy-24-oxo-5β-cholan-27-oic acid. The overall yield was 9%.

TABLE III

| | Physico-chemical properties | | | |
|---|---|---|---|---|
| | water solubility μmol/l | CMC mmol/l | rK' C-18 | pKa |
| UDCA | 19 | 19 | 0,4 | 5 |
| UCA | 1670 | 60 | 0,12 | 5 |
| 24-PUDCA | 13 | 9 | 0,44 | 3,90 |
| 24-PUCA | 1800 | 28 | 0,20 | 3,85 |

Rk' = relative values

The main physico-chemical properties of 24-PUCA are reported in table III and compared with those of some related compounds such as UDCA, UCA and 24-PUDCA.

The water solubility of 24-PUCA is similar to that of UCA with values about 100 times higher than those of UDCA and 24-PUDCA: 24-PUCA is very soluble also in protonated form.

24-PUCA shows a mild detergency even if it is able to form micelle at a physiological concentration, like occurs in bile.

The lipophilicity of 24-PUCA is intermediate between UCA and UDCA.

pKa value is lower to than that of the natural analogues UCA and UDCA and similar to that of 24-PUDCA. 24-PUCA shows interesting physico-chemical properties due to the high solubility of the protonated form, to the mild detergency and to the low pKa value, the compound appears to have the requisites to be efficiently secreted into the bile without being previously conjugated; like occurs for UDCA or UCA.

For these reasons 24-PUCA seems useful to reduce the detergency of the bile and to induce a good choleretic effect.

24-PUCA is also characterized by a low CMpH value which can be important for a resistance to precipitation at low pH values so assuring a good intestinal absorption.

24-PUCA appeared quite stable to 7-dehydroxylation in presence of anaerobic flora.

We claim:
1. 3α-7β-12α-trihydroxy-24-oxo-5β-cholan-27-oic acid.

* * * * *